(12) United States Patent
Kazravan

(10) Patent No.: US 8,707,961 B1
(45) Date of Patent: Apr. 29, 2014

(54) INTEGRATED SURGICAL REFUSE CONTAINER AND MAYO STAND COVER

(75) Inventor: Saba Jazmin Kazravan, Miami Beach, FL (US)

(73) Assignees: Saba Jazmin Kazravan, Miami Beach, FL (US); Kambiz Hassanzadeh, Miami Beach, FL (US)

( * ) Notice: Subject to any disclaimer, the term of this patent is extended or adjusted under 35 U.S.C. 154(b) by 16 days.

(21) Appl. No.: 13/236,946

(22) Filed: Sep. 20, 2011

Related U.S. Application Data

(63) Continuation-in-part of application No. 11/946,920, filed on Nov. 29, 2007, now abandoned.

(51) Int. Cl.
*A61B 19/00* (2006.01)
*A61B 19/08* (2006.01)

(52) U.S. Cl.
USPC .......................................... 128/849; 128/852

(58) Field of Classification Search
USPC ......... 128/849, 850, 851, 852, 853, 854, 855, 128/856, DIG. 24, 15; 383/33, 63, 65; 604/357
See application file for complete search history.

(56) References Cited

U.S. PATENT DOCUMENTS

| 4,476,860 | A | | 10/1984 | Collins et al. | |
|---|---|---|---|---|---|
| 5,170,804 | A | * | 12/1992 | Glassman | 128/849 |
| 5,388,593 | A | | 2/1995 | Thomalla | |
| 6,213,124 | B1 | * | 4/2001 | Butterworth | 128/853 |
| 6,308,875 | B1 | * | 10/2001 | Almo | 224/660 |

* cited by examiner

*Primary Examiner* — Patricia Bianco
*Assistant Examiner* — Ophelia A Hawthorne
(74) *Attorney, Agent, or Firm* — Malin Haley DiMaggio & Bowen, P.A.

(57) ABSTRACT

A Mayo stand cover and integrated medical waste refuse container that includes a pair of thin plastic sheets sealed together to cover the top and bottom of a Mayo stand with a liquid barrier and a strategically positioned, substantially rectangular visually clear sealable plastic refuse container sheet attached in a specific area of the Mayo stand cover to be positioned vertically perpendicular to the Mayo stand. The refuse container allows surgical personnel direct access for disposing of surgical waste and a visual opportunity to determine what has been placed in the refuse bag for counting purposes, and prevents waste material from falling out during removal of the Mayo stand cover after surgery.

1 Claim, 2 Drawing Sheets

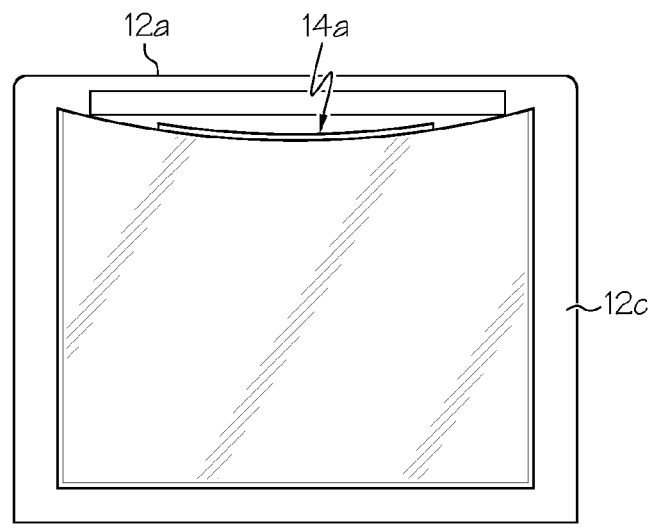
FIG. 2
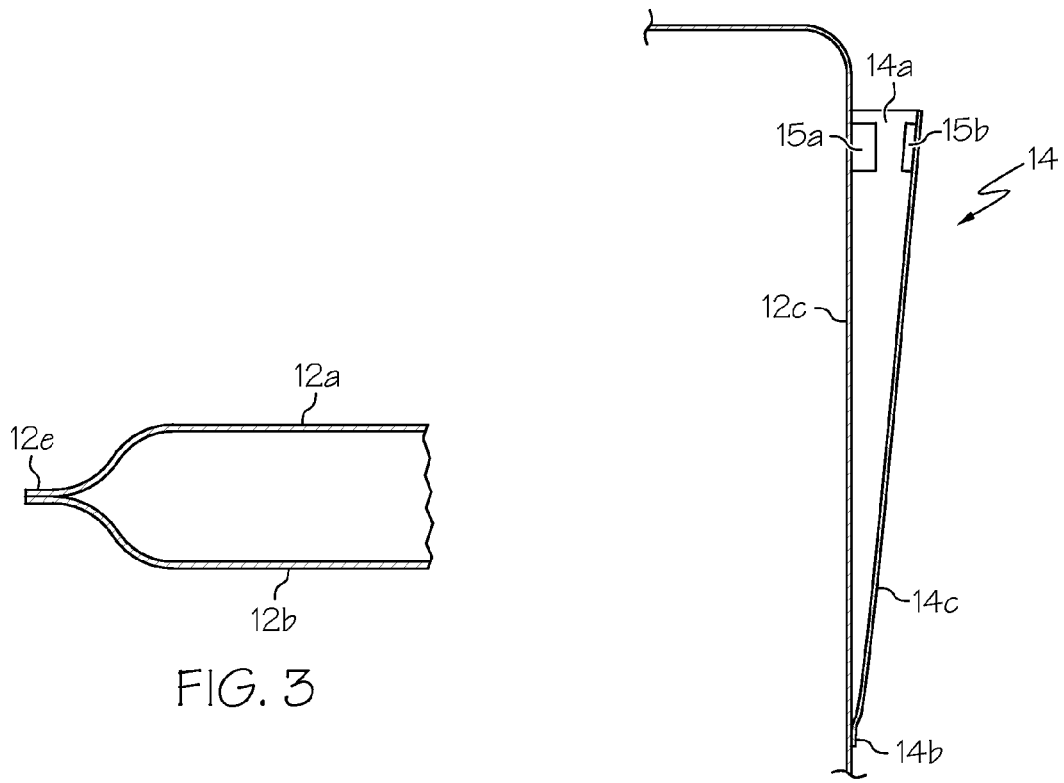
FIG. 3
FIG. 4

INTEGRATED SURGICAL REFUSE CONTAINER AND MAYO STAND COVER

CROSS REFERENCE TO RELATED APPLICATIONS

The present application is a continuation-in-part of U.S. patent application Ser. No. 11/946,920, filed on Nov. 29, 2007 now abandoned, the disclosure of which is incorporated herein by reference.

BACKGROUND OF THE INVENTION

1. Field of the Invention

This invention relates to a Mayo stand cover with a sealable surgical refuse container and, specifically, to the combination of a surgical refuse container and access slot and a Mayo stand cover that are used during surgical practices to aid in visually ascertaining disposal of surgical waste items that can be economically combined with a Mayo stand sterile cover.

2. Description of Related Art

The use of Mayo stands in surgery is well known. A Mayo stand is an adjustable horizontal table that is moved over a surgical table. The Mayo stand has a U-shaped frame with wheels. The table top has a vertical support arm at one end. The stand can be moved into place to extend over the surgical table. During a surgical procedure, the Mayo stand is covered by a disposable plastic bag that slides over the table top (above and below) of the Mayo stand and around the table top vertical support member. The plastic bag cover facilitates sterility while, at the same time, allowing for instruments or other devices to be placed on the top of the Mayo stand during intra-operative procedures.

U.S. Pat. No. 5,170,804 issued to Glassman on Dec. 15, 1992 shows a Mayo stand disposable drape. One of the drawbacks of the disposable drape as shown in the '804 patent is that surgical waste placed in floppy refuse bags can move outwardly during removal of the cover, potentially spilling the contents of the floppy bag, endangering the required sterile environment. Although the Glassman patent does show a separate but attached refuse pocket at the top edge of the Mayo stand, the pocket is not very practical for disposing of refuse due to its moveable structure and location, especially when the Mayo cover is removed from the Mayo table.

The present invention provides a non-complex, relatively inexpensive Mayo stand cover in combination with a clear plastic, low profile surgical waste and sterile trash slotted container for surgical refuse that is strategically positioned in a specific predetermined location along the vertical end of the Mayo stand so that all surgical waste deposits can be visible and clearly seen in the container. The refuse clear plastic container opening slot is flat and is located below the Mayo stand top surface. The refuse container is part of the Mayo cover and does not move outwardly or upwardly. The refuse slotted container is positioned to be accessed by the scrub nurse without having to in any way jeopardize or reduce the sterility or disturb the surgical instruments or other apparatus on the Mayo stand while disposing of waste. Most importantly, the bag can be sealed before removing the Mayo stand cover at the end of surgery.

SUMMARY OF THE INVENTION

A combined surgical waste slotted surface container and Mayo stand protective cover comprising a pair of thin plastic sheets that are joined together around the edges that are sized in length to cover the top and bottom surface of a Mayo stand table top and the Mayo stand vertical support, said thin plastic sheets providing a liquid barrier for deleterious organic materials that can be generated during surgery. A clear plastic surgical waste or trash container of a predetermined width and height is positioned substantially vertically along the Mayo cover next to the Mayo stand vertical support member at a predetermined distance from the top of the Mayo stand on the vertical side. The clear plastic surgical waste and sterile trash container sealable slotted opening is slightly below the top edge of the Mayo stand at the Mayo stand vertical support end. The distance from the top of the clear plastic refuse slotted container to the bottom of the clear plastic refuse container is predetermined for maximum utility by a scrub nurse that can deposit surgical waste and sterile trash into the clear plastic refuse container.

The Mayo stand cover is made of a pair of thin, flexible, liquid barrier plastic sheets and a clear plastic refuse transparent sheet which may be attached by an adhesive or by heat sealing to the Mayo cover outer surface. The Mayo cover is disposable so that after each surgical procedure, the entire device, including the Mayo stand cover and the combined refuse slotted container along with the surgical waste and sterile trash therein, is disposed of without danger of spillage because of the low profile of the slotted refuse container relative to the Mayo cover surface and the fact that the refuse container is part of the Mayo table cover and does not move outwardly when the cover is removed. The refuse container is not protruding outwardly, so it is out of all medical persons' way. It is sealed after surgery and before removal.

By providing a clear plastic refuse slotted compartment of a lower profile, the personnel during the surgical procedure, such as a scrub nurse, can easily identify each item of waste and trash that has been placed in the container of the medical surgical waste that is disposed during the surgical procedure. The slotted opening at the top of the refuse container is integrated strategically positioned below the Mayo stand table top when the cover is in place so that there is no possible interference between the disposal of surgical waste and trash and any of the surgical items placed on the top of the Mayo stand that are used for the surgical procedure such as surgical instruments, sponges or other important equipment.

To utilize the invention, the Mayo stand cover comprising the pair of plastic sheets, top and bottom, are manually slid over the top and bottom of the Mayo stand in its horizontal position and then continued down over the vertical member connected at one end to the Mayo stand until the plastic cover is draped basically to the very base of the Mayo stand. Typically, the Mayo stand base has a metal frame that is U-shaped with wheels. As the Mayo stand cover is in place, the integrated refuse container slotted opening is suspended a few inches below the top of the Mayo stand. The refuse container bottom can be located approximately one foot from the floor or any desired length. The clear transparent plastic single wall allows easy visual recognition of any surgical waste and sterile trash materials inside the refuse container especially for counting purposes. Once the surgical procedure is over, the refuse container is sealed, and the entire unit, including the Mayo stand cover and the integrated refuse container, can be removed from the Mayo stand without spillage and discarded in the appropriate manner for surgical trash.

It is an object of this invention to provide an improved cover for a Mayo stand for surgical procedures that provides a sterile environment around a Mayo stand and allows for the receipt of surgical waste and sterile trash during surgical procedures into a sealable refuse container. This will also allow the scrub nurse to keep all the intra-operative waste and trash nearby in a sterile manner for easy access without the help of other operating room personnel throughout the procedure.

In the absence of a refuse container, the scrub nurse must discard the intra-operative surgical waste into a waste basket located in the operating room. To discard the surgical waste and sterile trash into a waste basket, the scrub nurse must reach out by throwing the object into the basket. This action may cause cross contamination which then may lead to a "break in technique" and a break in sterility without intention which can be harmful to the patient. In an event of miscount, a person must carefully go through the entire waste basket to look for missing items. This can be time consuming which also can be harmful for the patient. In an event of a miscount, the medical procedure may be stopped until the missing item is found. Hence, all accountable sponges are thrown into the kick bucket for easy access for count. However, sometimes sponges are thrown into the waste basket accidentally by the scrub nurse. By having a visually clear sealable refuse container, those sponges can easily be identified while the medical procedure is in process. Therefore, the scrub nurse and the surgical team do not need to stop the procedure while the operating room personnel "circulating nurse" is searching in the waste basket across the room.

In accordance with these and other objects which will become apparent hereinafter, the instant invention will now be described with particular reference to the accompanying drawings.

BRIEF DESCRIPTION OF THE DRAWINGS

FIG. 2 shows a front elevational view of the integration of the refuse container and Mayo stand cover.

FIG. 3 shows a cross sectional view of the Mayo stand cover partially cut away along its top end showing two sheets of material.

FIG. 4 shows a side elevational cross sectional view of the refuse container showing the Mayo cover sheet of material and the single sheet of transparent plastic forming the refuse container.

PREFERRED EMBODIMENT OF THE INVENTION

Figure 1:
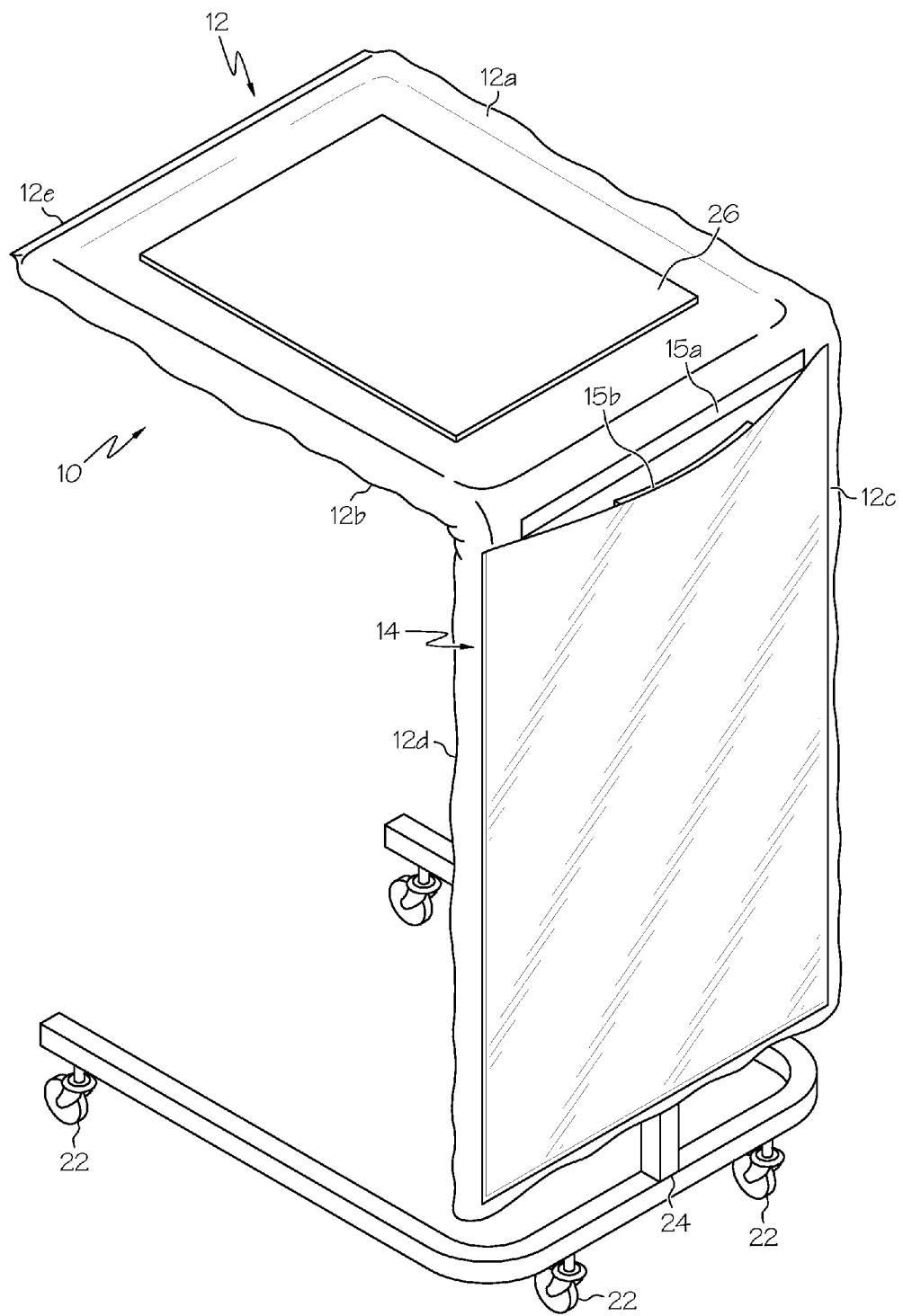
FIG. 1 shows a perspective view of the integrated refuse container and Mayo stand cover in accordance with the present invention.

Referring now to the drawings and, in particular, to FIG. 1, the device is shown generally at 10 comprised of a Mayo stand cover 12 that is shown in FIG. 1 in position covering a Mayo stand 20. Firmly attached on three sides to the vertical outside side of cover 12 is a clear plastic sheet forming a refuse container 14 that is attached either adhesively or heat sealed to the outside surface of upper plastic sheet 12c. A sealable closure such as hook and pile fasteners are mounted on each side of the container slot shaped opening. The refuse container 14 is strategically sized in a predetermined height, width and thickness and at a specific location a few inches below the upper surface of the Mayo stand to allow maximum efficiency for the personnel who are disposing of surgical waste or sterile trash manually into the refuse container 14. Note that any trash or refuse in container 14 can be seen by personnel in the surgical area because the container wall is visually clear plastic. The size and height of the refuse container 14 also is to preserve a sterile line surrounding the entire area and access by personnel, so that in depositing surgical waste, medical waste or sterile trash, there is no interference with any of the surgical instruments or equipment that would be disposed on top of the Mayo stand during the operation. Note that the typical Mayo stand is positioned over a surgical table to provide instruments needed during surgery. Thus, the refuse container 14 is integrated at a particular location with respect to the Mayo stand vertical support 24 because of the location of where the various personnel stand during the surgery.

The surgical Mayo stand cover 12 includes a first plastic sheet 12a that is uniformly connected as with the single piece terminating in the vertical side portion 12c so that it forms the top sheet of the cover 12. A bottom sheet is comprised of sheet 12b and terminates at 12d along the vertical side. The top and bottom sheets that form cover 12 are sealed along their edges to form a sterile enclosure and seal the long edge 12e which fits conveniently over the Mayo stand as a unit extending downwardly vertically above the floor. The base of the Mayo stand is shown including a frame 20 and wheels 22 and the vertical support member 24.

The refuse container 14 includes a sealable slot shaped opening 14a wherein the refuse is placed during surgery. Container opening 14a is strategically located at a certain distance along the cover 12 in its position during surgery. The container opening 14a is sealable with hook and pile fastener strips 15a and 15b attached to sheet 12c and 14c. The visually clear plastic surgical waste container 14 sheet which provides a liquid barrier may be glued or heat sealed to the outside surface of cover 12 at a specific location.

FIG. 2 shows the location from a vertical end view relative to the top cover 12a of the Mayo stand cover and the end vertical location of the refuse container 14 relative to top sheet 12c of the cover.

FIG. 3 shows the construction of the cover 12 which includes the top sheet 12a and bottom plastic sheet 12b heat sealed along the seam 12e that is used at the top of the Mayo stand for providing a sterile environment.

FIG. 4 shows a construction of the integrated refuse container 14 being made up of one sheet 14b heat sealed along the bottom at 14b to cover 12c and having the opening 14a. The material is a visually clear plastic and provides liquid barrier protection and is sized based on the refuse to be easily placed inside.

By use of the Mayo stand cover having an integrated sealable surgical waste refuse container, the cost of protecting the Mayo stand and providing for disposable waste and trash is greatly reduced. The safety and convenience is also provided by allowing for sealable clear plastic refuse containers that allow for easy visual identification of all medical waste contained inside especially for counting purposes. A single unit can be easily placed over a Mayo stand before surgery and easily disposed of after surgery in a convenient and safe way without waste spillage.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A Mayo stand cover and integrated surgical waste refuse container comprising:
   a Mayo stand cover that covers a Mayo stand the Mayo stand vertical support, comprising a pair of thin rectangular plastic liquid barrier sheets sealed together on three side edges to form a plastic bag with one open end to cover a top and bottom of the Mayo stand and the Mayo stand vertical support; and a visually clear sealable plastic rectangular surgical waste refuse sheet having a top opening just below the Mayo stand upper horizontal surface forming a waste container for receiving surgical waste and sterile trash, said waste container is attached via heat sealed to an outside of an upper surface of the plastic bag wherein the top opening of the waste container is located below an upper surface of the Mayo stand and the waste container extends downwardly covering substantially the entire Mayo stand vertical support member;

said visually clear sealable plastic surgical waste container having an opening extending laterally, said opening is sealable with hook and pile fastener strips, said hook fastener is mounted on an exterior surface of said Mayo cover just below the upper surface of said Mayo stand, and said pile fastener is mounted on an inside top edge of the plastic sheet container opening and positioned to engage the hook fastener when the waste container opening is closed completely sealing the container opening.

\* \* \* \* \*